United States Patent
Dickenson et al.

(10) Patent No.: US 6,364,902 B1
(45) Date of Patent: Apr. 2, 2002

(54) METAL COMPOSITE TUBE FOR BIOMEDICAL APPLICATIONS

(75) Inventors: Roger C. Dickenson; John Freeland, both of Roanoke, VA (US)

(73) Assignee: Noble-Met, Ltd., Salem, VA (US)

( * ) Notice: Subject to any disclaimer, the term of this patent is extended or adjusted under 35 U.S.C. 154(b) by 0 days.

(21) Appl. No.: 09/167,104

(22) Filed: Oct. 5, 1998

(51) Int. Cl.[7] .................................................. A61F 2/06
(52) U.S. Cl. ..................... 623/1.15; 623/1.34; 623/1.27
(58) Field of Search ......................... 623/1, 12, 1.15, 623/1.34, 1.27, 1.18, 1.33

(56) References Cited

U.S. PATENT DOCUMENTS

| | | | | |
|---|---|---|---|---|
| 3,618,614 A | * | 11/1971 | Flynn | 623/1.34 |
| 5,047,050 A | * | 9/1991 | Arpesani | 623/1 |
| 5,289,831 A | * | 3/1994 | Bosley | 128/899 |
| 5,320,100 A | * | 6/1994 | Herweck et al. | 623/1 |
| 5,607,442 A | * | 3/1997 | Fischell et al. | 623/1 |
| 5,628,787 A | * | 5/1997 | Mayer | 623/1 |
| 5,725,572 A | * | 3/1998 | Lam et al. | 623/1 |
| 5,735,897 A | * | 4/1998 | Buirge | 623/1.34 |
| 5,759,174 A | * | 6/1998 | Fischell et al. | 623/1 |
| 5,873,904 A | * | 2/1999 | Ragheb et al. | 623/1 |
| 5,873,907 A | * | 2/1999 | Frantzen | 623/1 |
| 6,190,303 B1 | * | 2/2001 | Glenn et al. | 600/3 |
| 6,200,338 B1 | * | 3/2001 | Solomon et al. | 623/1.34 |
| 6,203,732 B1 | * | 3/2001 | Clubb et al. | 264/81 |
| 6,206,915 B1 | * | 3/2001 | Fagan et al. | 623/1.42 |

* cited by examiner

Primary Examiner—David H. Willse
Assistant Examiner—Suzette J. Jackson
(74) Attorney, Agent, or Firm—Bryan D. Wright; Fred Rosenbaum

(57) ABSTRACT

Metal composite tubes offer advantages in constructing biomedical device components such as stents. The composite tube comprises a cylindrical wall made of a biocompatible metal matrix with a filament or filaments of other metals that add radiopacity, and/or other advantageous mechanical or physical properties. The filaments are generally oriented along the length of the tube and are surrounded by the wall of the tube.

9 Claims, 1 Drawing Sheet

METAL COMPOSITE TUBE FOR BIOMEDICAL APPLICATIONS

BACKGROUND OF THE INVENTION

This invention relates generally to tubes used in medical devices, particularly stents.

Stents, used for reopening and maintaining patent lumens in natural conduits, are made from slotted tubing. Slotted tube stents are expandable, in situ, by dilators, such as balloons. Usually, the unexpanded stent is placed over a deflated balloon which is located on the end of a catheter. The catheter is then inserted into the body with the balloon and stent positioned in the constricted area of the conduit. The balloon is then inflated to expand the stent into contact with the interior wall of the conduit thereby opening the constricted area. The balloon is subsequently deflated and the catheter is removed leaving the stent in place in the enlarged opening. Such stents are implanted in the vascular, digestive and urinary systems, or in any orifice or lumen, to hold the site open and reinforce the wall of the orifice.

Examples of such tubes and devices can be found in U.S. Pat. Nos. 5,679,470; 5,630,840; 5,628,787; 5,213,111; 5,725,570; 2,947,078; 2,215,477 and 2,371,348. Also there is a PCT document, WO 93/19803, concerning filled wires. Other publications include, Handbook of Precious Metals, Savitskii, Hemisphere Publishing Co. 1989 on the subject of hydrostatic extrusion and manufacturing of clad metals and composites, specifically for RF cables, and Metals Handbook, 9th Ed. Vol. 14, "Forming and forging", ASM International, 1988, Chapter on Wire, Rod and Tube Drawing.

Slotted tube stents may be made from stainless steel, nickel or cobalt based alloys, or nitinol. However, these stents exhibit poor visibility under fluoroscopy. In some cases, separate radiopaque markers are required for adequate visibility.

It is of critical importance to the accurate placement of the stent to be able to visually place the stent in the area of the constriction.

This shortcoming has been addressed in stents braided from wire. The approach was to braid the stents from composite wire, wherein the wire is comprised of an outer layer of high strength material and an inner core of a radiopaque material. However, no such approach has been available for stents made from slotted metal tubing.

Two approaches are available for enchancing the radiopacity of stents made from metal tubing. One approach is to use a layered composite tube i.e., one tube layered on top of another. If one of the layers were radiopaque, the composite tube stent would have improved radiopacity. Another approach is to use filaments of a radiopaque material embedded in the cylindrical wall of the tube. In either case, what is needed is a composite tube that offers strength, biocompatibility, and radiopacity.

SUMMARY OF THE INVENTION

One embodiment of the present invention includes a composite tube for a stent, said tube having one or more filaments [or layers] of radiopaque material within the wall of a high strength, biocompatible tube. The filaments [or layers] are preferably parallel to the axis of the tube, and they may be distributed in any pattern advantageous to the properties of the stent. The filaments are preferably tantalum, but they could also be any other radiopaque and biocompatible material like platinum, gold, or another high Z material (heavy metals) or alloys of these materials. The matrix of the tube is preferably stainless steel, but it may also be a nickel, cobalt, or titanium based alloy or a nickel-titanium shape memory alloy. A pattern of slots can be cut into the composite tube. The form produced, comprising an alternating pattern of solid material and slots, imparts the property of expandability by radial force, to the tube.

In another embodiment of the present invention, the filaments are a highly conductive material (e.g. silver, gold, copper, or aluminum). The filaments improve the electrical and thermal conductivity of the tube. This enhances the use of the tube as an electrode in a biomedical device such as an electrophysiology catheter.

In another embodiment of the present invention, the filaments are a material that enhance the mechanical properties of the tube. For example, nickel-titanium shape memory filaments would improve the kink resistance of the tube.

In another embodiment of the present invention, one or more of the filaments are removed, thereby leaving an open lumen within the tube wall. An external wire could be inserted in this open lumen and welded, soldered or crimped in place. This provides an advantageous way of attaching wires to a tube. This lumen can also be used for infusion of fluids such as pharmacological agents for therapeutic purposes or saline for flushing a treatment site. In another embodiment of the present invention, the filaments are a shape other than round, and/or the tube is a shape other than round.

DESCRIPTION OF THE PREFERRED EMBODIMENT

The principles of the invention will now be described using the drawings and specific language. However, no limitation of the scope of the invention is thereby intended. Many alterations, modifications, and further applications are contemplated as would normally occur to one skilled in the art.

Figure 1:
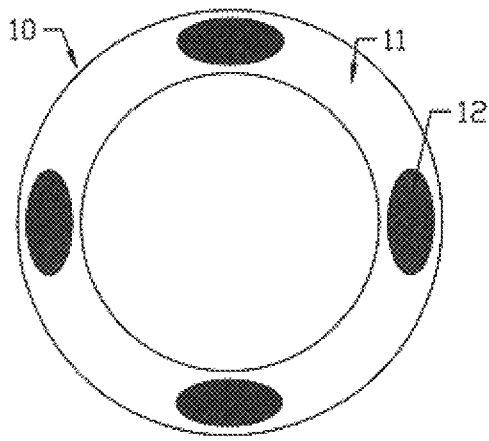
FIG. 1 is a cross section of a composite tube according to the preferred embodiment of the present invention.

Referring to FIG. 1, there is shown a composite tube 10 according to the preferred embodiment of the present invention. This composite tube 10 includes matrix tube 11 and a multiple filaments 12. The matrix tube 11 is made, preferably, of stainless steel, but it may also be a nickel, cobalt, or titanium based alloy or a nickel-titanium shape memory alloy. The filaments 12 are preferably tantalum, but they may also be platinum, gold, tungsten, including alloys of these materials. This configuration has the advantage that the filament is entirely surrounded by the continuous matrix material except where the tube is cut. Also, the cross-section of the filaments is not circular. The filaments may have virtually any cross-sectional shape. Furthermore, each filament need not be the same material. For example, one could be tantalum to add radiopacity, and another could be silver to add electrical conductivity.

Figure 2:
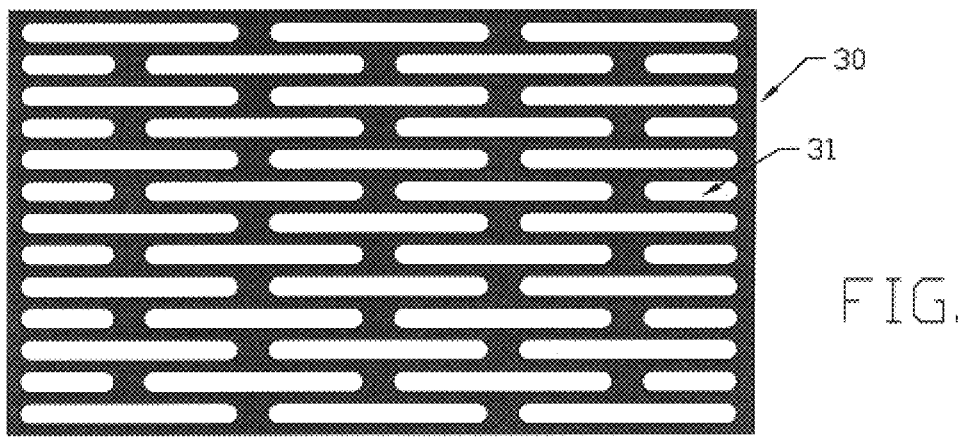
FIG. 2 is a plan view of a portion of a slotted stent, before expansion, made from a composite tube according to one embodiment of the present invention.

Referring to FIG. 2, there is shown a stent 30 made from a composite tube such as described in FIG. 1. The tube has been cut to a length appropriate for a stent, approximately 1 mm to 50 mm. Slots 31 have been cut through the wall in a parallel interrupted pattern that allows the stent to be expanded in-situ by a balloon positioned inside the tube. Such a stent would deploy similar to a non-composite tube stent, but the radiopaque filaments, such as filaments 12 in FIG. 1, would improve the imaging of the stent under a fluoroscope.

Figure 3:
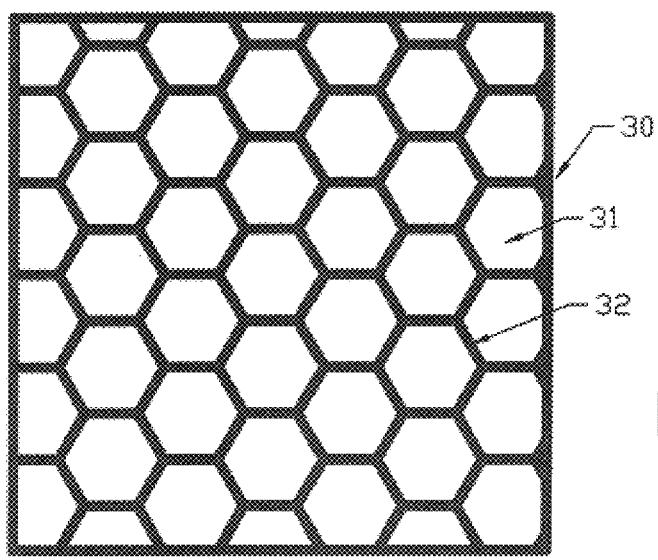
FIG. 3 is a plan view of the slotted stent of FIG. 2 after expansion.

Referring to FIG. 3, there is shown the stent 30, described in FIG. 2, after balloon expansion. The expanded stent has aperatures 31 defined by the edges of the slots. Some of the filaments (not shown) have been partially removed by the slots, but in the bridges 32 between the slots the filaments are still surrounded by the wall of the matrix tube. Thus, the filaments (not shown) are always anchored within the matrix, and even after expansion are held in place. Further, if the slots are cut at an angle to the longitudinal tube axis (not shown), the filament area exposed by the slots could be further reduced.

The illustration and foregoing description of the invention is considered to be illustrative and not restrictive in character. Only the preferred embodiment has been shown and described, protection for all changes and modifications that come within the spirit of the invention is desired.

We claim:

1. An elongated metal tube for use as a stent in surgical procedures comprising a solid high strength biocompatible cylindrical metal wall surrounding a central longitudinal bore, said solid high strength biocompatible cylindrical metal wall being made from one of the group consisting of stainless steel, nickel based alloy, cobalt based alloy, titanium based alloy or nickel titanium shape memory alloy, said solid high strength biocompatible cylindrical metal wall having a plurality of lumen within said wall extending longitudinally along said wall parallel to said central longitudinal bore, a radiopaque metal filament disposed in at least one of said lumen, said radiopaque metal filament being made from one of the group consisting of tantalum, platinum, gold, tungsten and alloys based on these metals.

2. An elongated metal tube for use as a stent in surgical procedures as claimed in claim 1 herein a highly conductive metal filament is disposed in at least one of said plurality of lumen, said highly conductive metal filament made from one of the group consisting of silver, copper, and alloys of these metals, said highly conductive metal filament providing electrical and thermal conductivity in said elongated metal tube.

3. An elongated metal tube for use as a stent in surgical procedures as claimed in claim 1 wherein a nickel-titanium shape memory alloy filament is disposed in at least one of said lumen.

4. An elongated metal tube for use as a stent in surgical procedures as claimed in claim 1 wherein at least one of said lumen provides a passageway for infusion of pharmacological agents therethrough.

5. An elongated tube for use as a stent in surgical procedures as claimed in claim 1 wherein a pattern of slots is cut through said solid high strength cylindrical metal wall, said slots permitting radial expansion of said elongated tube.

6. An elongated tube for use as a stent in surgical procedures comprising a high strength biocompatible metal wall surrounding a central bore, said wall having a plurality of longitudinal lumen formed therein, at least one of said lumen having a radiopaque metal filament disposed therein, at least one of said lumen having a highly conductive metal filament therein for applying electrical or thermal energy thereto, and at least one of said lumen providing a passageway for pharmacological agents.

7. An elongated tube for use as a stent in surgical procedures as claimed in claim 6 wherein a shape memory metal alloy is disposed in at least one of said lumen.

8. An elongated tube for use as a stent in surgical procedures as claimed in claim 7 wherein a pattern of slots is formed through said solid wall permitting radial expansion of said elongated tube.

9. An elongated tube for use as a stent in surgical procedures as claimed in claim 6 wherein a pattern of slots is formed through said solid wall, said slots permitting a the radial expansion of said elongated tube.

* * * * *